United States Patent
Haddadi (10) Patent No.: US 9,195,077 B2
(45) Date of Patent: Nov. 24, 2015

(54) DEVICE FOR MEASURING A CHARACTERISTIC READING DISTANCE OF AN INDIVIDUAL

(75) Inventor: Ahmed Haddadi, Charenton-le-Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 756 days.

(21) Appl. No.: 13/113,119

(22) Filed: May 23, 2011

(65) Prior Publication Data

US 2011/0295117 A1    Dec. 1, 2011

(30) Foreign Application Priority Data

May 25, 2010    (FR) ...................................... 10 02200

(51) Int. Cl.

| | |
|---|---|
| G01S 15/00 | (2006.01) |
| A61B 3/00 | (2006.01) |
| G02C 13/00 | (2006.01) |
| G01S 15/88 | (2006.01) |
| A61B 3/032 | (2006.01) |
| A61B 8/00 | (2006.01) |

(52) U.S. Cl.
CPC .............. *G02C 13/003* (2013.01); *G01S 15/88* (2013.01); *A61B 3/0083* (2013.01); *A61B 3/032* (2013.01); *A61B 8/58* (2013.01); *A61B 2560/0431* (2013.01)

(58) Field of Classification Search
USPC .......................................................... 367/99
See application file for complete search history.

(56) References Cited

U.S. PATENT DOCUMENTS

| | | | | |
|---|---|---|---|---|
| 6,127,990 | A * | 10/2000 | Zwern ................................ 345/8 |
| 6,359,601 | B1 * | 3/2002 | Maguire, Jr. ....................... 345/7 |
| 6,452,870 | B1 * | 9/2002 | Breed et al. ...................... 367/99 |
| 6,603,491 | B2 * | 8/2003 | Lemelson et al. ............ 715/784 |
| 7,203,911 | B2 * | 4/2007 | Williams ....................... 715/864 |
| 2002/0105482 | A1 * | 8/2002 | Lemelson et al. ................ 345/7 |
| 2003/0210258 | A1 * | 11/2003 | Williams ....................... 345/700 |
| 2005/0211404 | A1 * | 9/2005 | Makkonen ..................... 162/198 |
| 2010/0066975 | A1 * | 3/2010 | Rehnstrom .................... 351/210 |
| 2010/0195051 | A1 * | 8/2010 | Murray et al. ................. 351/209 |
| 2011/0292345 | A1 * | 12/2011 | Haddadi ....................... 351/239 |

FOREIGN PATENT DOCUMENTS

JP       2000-325309 A    11/2000

\* cited by examiner

*Primary Examiner* — James Hulka
(74) *Attorney, Agent, or Firm* — Young & Thompson (57) ABSTRACT

A device for measuring a characteristic reading distance of an individual, includes a measurement support carrying at least one ultrasound emitter member and at least one ultrasound receiver member, at least one of these members, referred to as a main measurement member, possessing a measurement axis on which emission or reception by the main measurement member is privileged, and being suitable for emitting or receiving ultrasound propagating in a measurement cone centered on its measurement axis. The device further includes an electronic processor unit adapted, as a function of the ultrasound signal received by the receiver member, to deliver a signal representative of the distance between the measurement support and an eyeglass frame worn by the individual's head, and to deduce therefrom the characteristic reading distance, and elements to verify that the eyeglass frame is situated at least in part in the measurement cone of the main measurement member.

9 Claims, 4 Drawing Sheets

DEVICE FOR MEASURING A CHARACTERISTIC READING DISTANCE OF AN INDIVIDUAL

TECHNICAL FIELD TO WHICH THE INVENTION RELATES

The present invention relates to a device for measuring an individual's characteristic reading distance.

The invention also relates to a method of measuring such a distance by means of such a device.

TECHNOLOGICAL BACKGROUND

Determining the characteristic reading distance of an individual is very important for making ophthalmic lenses that provide their wearer with optical correction that is personalized and in particular that is adapted to the individual's near vision.

Document JP 2000-325309 discloses a device for determining such a characteristic distance and that comprises firstly a reading medium implemented in the form of a tablet placed at a distance suitable for reading text carried by said tablet, and secondly measurement means for measuring the distance of the head relative to the tablet. Those distance measurement means make use of ultrasound: an ultrasound emitter and an ultrasound receiver are provided on the tablet. The receiver detects the ultrasound that has been emitted by the emitter and reflected on the individual's head. That method presents the drawback of not being very accurate.

OBJECT OF THE INVENTION

An object of the present invention is to propose a device for measuring a characteristic reading distance that enables measurements to be performed quickly, accurately, and easily, putting as little constraint as possible on the individual's posture relative to a reading medium (and in particular on distance and inclination about the horizontal). In particular, it is desired to avoid the need to place an accessory on the individual's head or eyeglass frame in order to identify three-dimensional position.

To this end, the invention provides a device for measuring a characteristic reading distance of an individual, the device comprising a measurement support carrying at least one ultrasound emitter member and at least one ultrasound receiver member, at least one of these members, referred to as a main measurement member, possessing a measurement axis on which emission or reception by the main measurement member is privileged, and being suitable for emitting or receiving ultrasound propagating in a measurement cone centered on its measurement axis, the device being characterized in that it includes an electronic processor unit adapted, as a function of the ultrasound signal received by the receiver member, to deliver a signal that is representative of the distance between the measurement support and an eyeglass frame worn by the individual's head, and to deduce therefrom said characteristic reading distance, and means to verify that said eyeglass frame is situated at least in part in the measurement cone of said main measurement member.

The measurement is performed on a principle of measuring distance by ultrasound: the receiver member detects ultrasound signals emitted by the emitter and reflected on the eyeglass frame placed on the individual's head.

In particular, it is particularly advantageous to perform this method using ultrasound since the difference in reflectivity between the individual's skin and the eyeglass frame placed on the individual's head is large, thereby making it easy to distinguish the signal as reflected by the frame.

The characteristic reading distance is deduced from the distance between the individual's eyeglass frame and the measurement device.

Advantageously, the device includes a reading medium presenting a plane display portion suitable for displaying signs and the electronic processor unit is suitable for calculating said characteristic reading distance as being the distance between said reading medium and the eyeglass frame worn by the individual's head.

In order to take the measurement easily, it is advantageous to use an ultrasound emitter member emitting in a solid angle that easily covers all of the individual's head or at least the frame worn by the individual's head, i.e. emitting ultrasound over a measurement cone presenting an angle at the apex that is greater than or equal to 15 degrees.

In order to take a measurement that is accurate, it is advantageous to use a main measurement member that is directional, i.e. a member that emits or receives ultrasound exclusively within a measurement cone presenting an angle at the apex that is less than or equal to 45 degrees.

It is then useful to verify that the individual's head, and more precisely the eyeglass frame worn by the individual's head, does indeed lie in the measurement cone.

For this purpose, the measurement device includes means for verifying that the eyeglass frame is situated at least in part in the measurement cone of said main measurement member.

In a first embodiment of the device of the invention, the measurement device also advantageously includes a reading medium presenting a plane display portion suitable for displaying signs, and means for releasably mounting the measurement support on the reading medium.

For example, the reading medium may be constituted by a computer screen and the releasable mounting means are suitable for clipping the measurement support onto the screen.

The measurement support may then advantageously be fastened to various types of reading medium adapted to the individual, for example a comic strip for children, or a book, or a magazine, or any type of display screen.

In a second embodiment of the device of the invention, the measurement device advantageously further includes a reading medium that presents a plane display portion suitable for displaying signs, and means for releasably mounting the reading medium on the measurement support.

For example, said measurement support forms a docking station for the reading medium, the docking station including both a base suitable for standing in stable manner on a plane, and releasable mechanical connection means suitable for co-operating with complementary connection means of the reading medium. Advantageously, the connection means are such that, after connection, the plane of the display portion is oblique relative to the plane on which the base stands.

The reading medium may then be a portable appliance belonging to the individual, of the mobile telephone or multimedia tablet type.

Whatever the embodiment of the measurement device, said main measurement member may be mounted in stationary manner on said measurement support, or it may be movably mounted on said measurement support so as to be capable at least of pivoting relative to a pivot axis perpendicular to the measurement axis of said main measurement member.

Advantageously, the means for verifying that the individual's head is situated at least in part in the measurement cone of said main measurement member include visual detection means operating on the parallax principle to enable the individual to detect visually a position of the individual's head relative to the main measurement member in which the head is situated at least in part in the measurement cone of said main measurement member.

By way of example, these verification means comprise at least one target and at least one mark secured to said main measurement member, the mark and the target being offset from each other in the direction of the measurement axis of the main measurement member. The individual's head is situated at least in part in the measurement cone of the measurement member when the individual can see that said target is centered on said mark.

In a variant, the verification means include, for example, at least one target secured to said main measurement member and located at the end of a cavity such that the target can be seen by the individual only within a predetermined range of angles of orientation of the measurement member relative to the individual's head.

When said main measurement member is movably mounted on said measurement support, the means for verifying that the individual's head is situated at least in part in the measurement cone of said main measurement member include automatic detection means for automatically detecting a position of the individual's head relative to the main measurement member in which the head is situated at least in part in the measurement cone of said main measurement member.

The automatic detection means then include means for causing said main measurement member to scan through a range of angular positions relative to the measurement support, and means for determining the angular position of said main measurement member that corresponds to a received ultrasound signal of maximum intensity or intensity greater than a threshold.

Advantageously, the measurement device includes a reading medium presenting a plane display portion suitable for displaying signs, and mechanical means for ensuring the position of the reading medium relative to the measurement support is unchanging, and in which the electronic processor unit is suitable for calculating said characteristic reading distance as a function of said unchanging position.

The electronic processor unit is then suitable for deducing the looked-for characteristic reading distance corresponding to the distance between the individual's eyeglass frame and the reading medium from the distance as measured between the measurement support and the individual's eyeglass frame, and from the known position of the measurement support relative to the reading medium.

Alternatively, the measurement device includes means or determining the position of the reading medium relative to the measurement support in a measurement direction.

The electronic processor unit is then suitable for deducing the looked-for characteristic reading distance corresponding to the distance between the individual's eyeglass frame and the reading medium from the distance measured between the measurement support and the individual's eyeglass frame and from the determined position of the measurement support relative to the reading medium.

In particular, the means for determining the relative position of the reading medium comprise means for measuring an angle of inclination of the measurement support relative to the horizontal and means for measuring the distance between the measurement support and the reading medium.

According to another advantageous and non-limiting characteristic of the measurement device, the device includes a reading medium presenting a plane display portion suitable for displaying signs, and an electronic processor unit suitable for controlling the reading medium to modify the size of the signs displayed as a function of the determined characteristic reading distance.

The comfort of the individual is thus increased and the accuracy of the measurement is improved: the individual can occupy a reading position that the individual finds natural more easily.

According to another advantageous and non-limiting characteristic of the measurement device, the receiver member includes a receiver element placed inside a conical cavity presenting an angle at the apex lying in the range 15 degrees to 45 degrees, and at a depth of at least 30 millimeters.

The conical cavity constitutes the waveguide for emitting and receiving ultrasound and serves to amplify the received signal. Measurement accuracy is thus improved.

DETAILED DESCRIPTION OF AN EMBODIMENT

The following description made with reference to the accompanying drawings given by way of non-limiting example makes it clearly understood what the invention consists in and how it can be reduced to practice.

In the description below, the optician determines the reading distance that is characteristic of an individual.

As shown in FIGS. 7, 9, 10, and 11, an individual's head 10 is fitted with an eyeglass frame 30 having ophthalmic lenses for correcting vision.

The individual may be sitting or standing.

The vertical direction is defined herein as being the direction given by a plumb line at a determined location. A horizontal direction is perpendicular to the vertical direction.

A sagittal plane PSAG of the individual's head 10 is a midplane of the individual's head passing halfway between the two centers of rotation of the individual's eyes 20 and perpendicular to the straight line interconnecting those two centers of rotation of the eyes 20. The sagittal plane is substantially vertical when the individual is sitting or standing in a natural posture.

A gaze direction DR is defined as the straight line bisecting the angle between the lines connecting each of the individual's eyes to the points on which the individual's gaze is fixed.

A gaze plane PR is likewise defined as being perpendicular to the gaze direction DR. To a first approximation, the gaze plane PR coincides with the mean plane PM of the frame 30.

The mean plane PM of the eyeglass frame 30 in this example coincides with the mean planes of the corresponding ophthalmic lenses.

Figure 8:
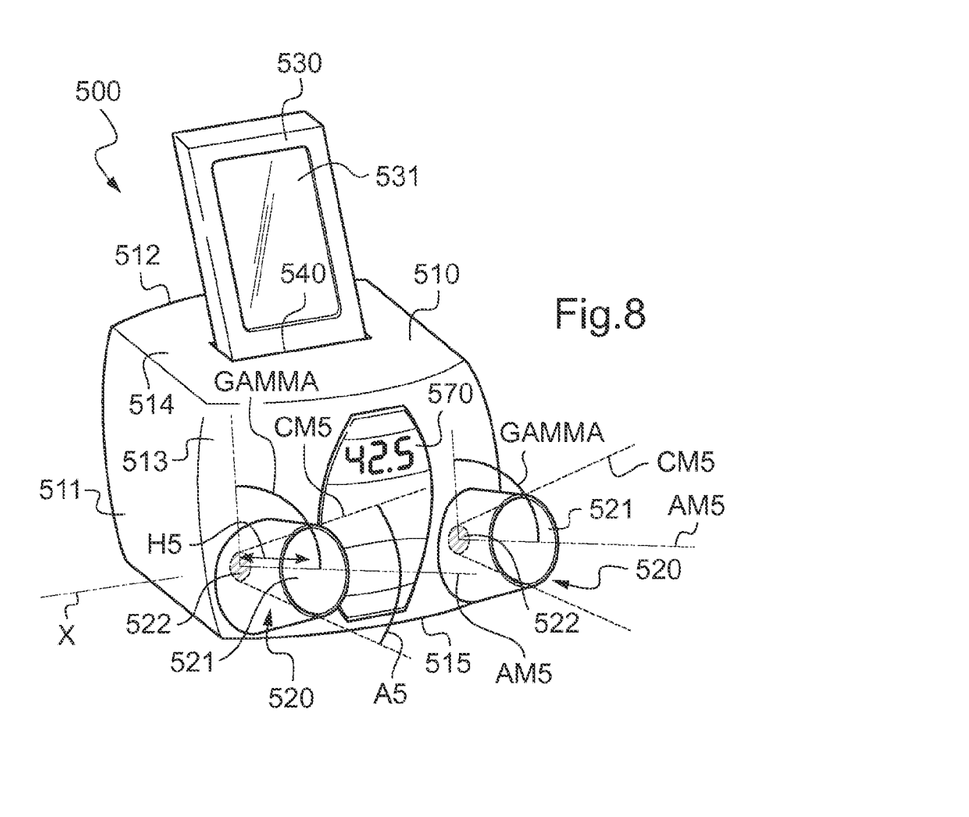
FIG. 8 is a front perspective view of a first variant of a second embodiment of the measurement device of the invention.

FIGS. 1 to 6 show different variants of a first embodiment of the measurement device 100, 200, 300, 400 of the invention, and FIG. 8 shows a second embodiment of the device 500 of the invention.

This measurement device 100, 200, 300, 400, 500, 600 includes a measurement support 110, 210, 310, 410, 510 carrying at least one ultrasound emitter member and at least one ultrasound receiver member.

The measurement support 110, 210, 310, 410, 510, 610 comprises a box 111, 211, 311, 411, 511, 611 of generally rectangular shape with a top face 114, 214, 314, 414, 514 and an opposite bottom face 115, 215, 315, 415, 515.

The box 111, 211, 311, 411, 511, 611 has two emitter-receiver members 120, 220, 320, 420, 520, 620.

These emitter-receiver members are accessible from the front face 113, 213, 313, 413, 513 of the box.

This front face faces towards the individual's head.

Each emitter-receiver member 120, 220, 320, 420, 520, 620 possess an axis AM1, AM2, AM3, AM4, AM5 that is suitable for emitting or for receiving ultrasound propagating in a measurement cone CM1, CM2, CM3, CM4, CM5 centered on the measurement axis.

Each emitter-receiver member 120, 220, 320, 420, 520, 620 comprises an emitter-receiver element 122, 222, 322, 422, 522 that is suitable for emitting and receiving ultrasound. The emitter-receiver element is placed at the end of a cavity 121, 221, 321, 421, 521 formed in the box. The cavity 121, 221, 321, 421, 521 in these examples presents an inside wall 121, 221, 321, 421, 521 that is conical in shape.

The term "measurement axis" is used herein to mean an axis along which emission or reception by the measurement member is privileged.

For an emitter-receiver member, the measurement axis corresponds to the axis along which a signal of maximum intensity is detected for an emitted signal of determined intensity.

For a receiver member, the measurement axis corresponds to the axis passing through the receiver element on which the intensity of the received ultrasound signal is at a maximum when said axis is pointing to an ultrasound source. For an emitter member, the measurement axis corresponds to the axis passing through the emitter element on which the intensity of the emitted ultrasound signal is at a maximum when said axis is pointing to an ultrasound receiver element.

In practice, the measurement axis corresponds to an axis of symmetry of the cavity 121, 221, 321, 421, 521 of the measurement member. In these examples, the measurement axis corresponds to the axis of revolution of the conical cavity 121, 221, 321, 421, 521.

The measurement axes AM1, AM2, AM3, AM4, AM5 of the emitter-receiver members 120, 220, 320, 420, 520, 620 are parallel to each other in these examples.

In a variant, it is possible to envisage the measurement axes not being parallel to each other. Inclining them may serve to take account of a strongly curved eyeglass frame being worn by the individual.

It is particularly advantageous to use a measurement member that includes a conical cavity having a measurement element located at the end thereof, since the conical cavity then acts as a waveguide and contributes to amplifying the signal.

More precisely, each emitter-receiver member 120, 220, 320, 420, 520, 620 in these examples comprises an emitter-receiver element 122, 222, 322, 422, 522 placed inside a conical cavity 121, 221, 321, 421, 521 presenting an angle at the apex A1, A2, A3, A4, A5 that lies in the range 15 degrees to 45 degrees, being located a depth H1, H2, H3, H4, H5 of at least 30 millimeters.

The angle at the apex of the measurement cone of each emitter-receiver member is the result of a compromise between having an aperture that is sufficiently large to emit ultrasound towards all of the individual's face, so as to make it easy to cover the individual's eyeglasses, and an aperture that is restricted so as to receive only ultrasound that is reflected by the individual's head, and mainly by the individual's eyeglasses.

The measurement cone of the measurement member designates a solid angle representing the set of ultrasound propagation axes in three dimensions along which ultrasound is emitted or received by the measurement member. The solid angle is centered on the measurement axis and corresponds substantially to the solid angle defined by the conical cavity.

The emitter-receiver members 120, 220, 320, 420, 520 are aligned on a straight line parallel to the top and bottom faces of the box of the measurement support.

More precisely, the two emitter-receiver members in these examples are spaced apart by 7 centimeters. This spacing enables each emitter-receiver member to be placed facing one of the ophthalmic lenses of the individual's eyeglass frame 30.

Figure 4:
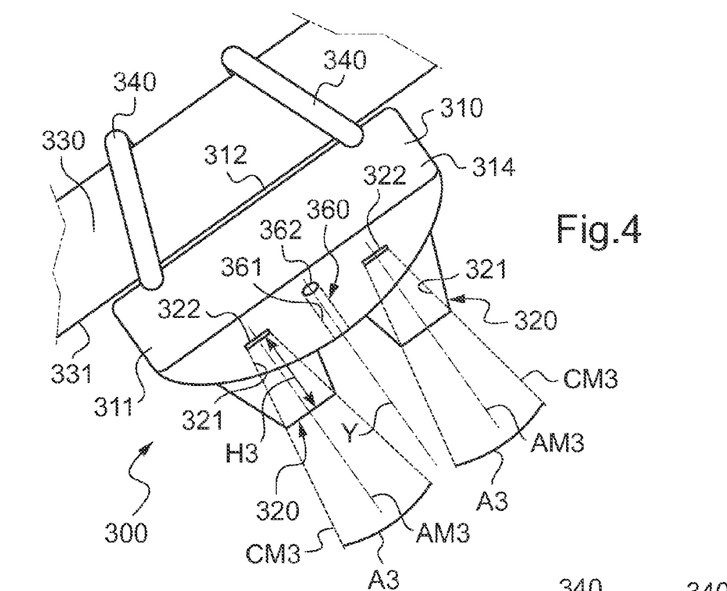
FIG. 4 is a plan view of a second variant of the FIG. 1 measurement device.
Figures 5, 6:
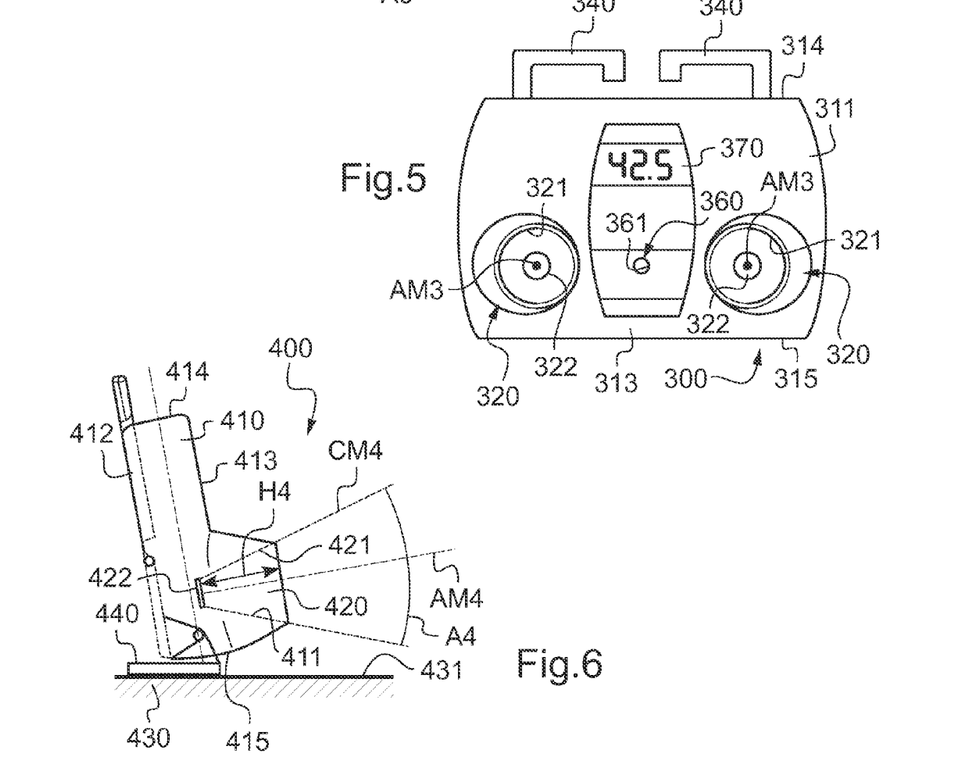
FIG. 5 is a face view of the FIG. 4 measurement device.
FIG. 6 is a profile view of a third variant of the FIG. 1 measurement device.
Figure 7:
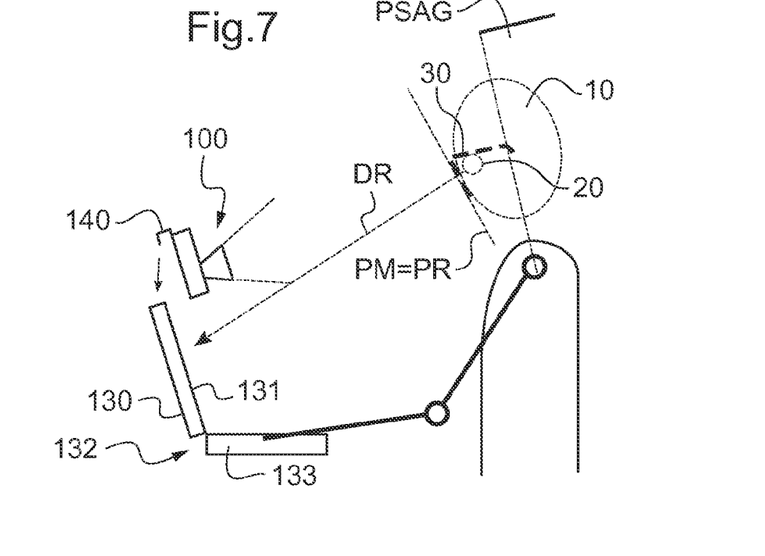
FIG. 7 is a diagrammatic view of an individual using the device of any of FIGS. 1 to 5.

In a first embodiment of the measurement device 100, 200, 300, 400 and variants thereof, the device also has a reading medium 130, 330, 430 presenting a plane display portion 131, 331, 431 suitable for displaying signs, as shown in FIGS. 4, 6, and 7. The measurement device 100, 200, 300, 400 also has means 140, 240, 340, 440 for releasably mounting the measurement support 110, 210, 310, 410 on the reading medium 130, 330, 430.

The rear face 112, 212, 312, 412 of the box 111, 211, 311, 411 of the measurement support 110, 210, 310, 410 is advantageously plane in order to make it easy to mount the measurement support on the reading medium.

In the example shown in FIG. 7, the reading medium 131 is constituted by a screen of a laptop computer 132 having its screen 130 hinged to a keyboard 133. The releasable mounting means 140 are suitable for clipping the measurement support onto the screen 130.

In a variant, the reading medium may be a book, a display screen other than a computer screen, or a tablet including optotypes, for example.

Figure 1:
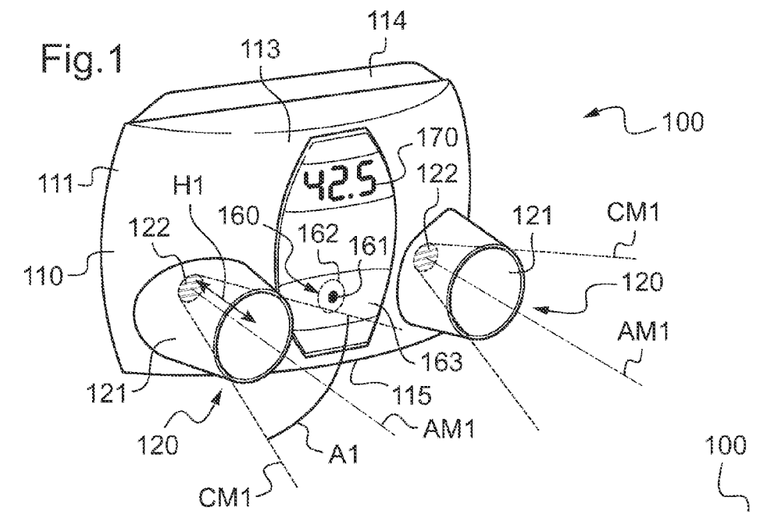
FIG. 1 is a front perspective view of a first embodiment of the measurement device of the invention.
Figures 2, 3:
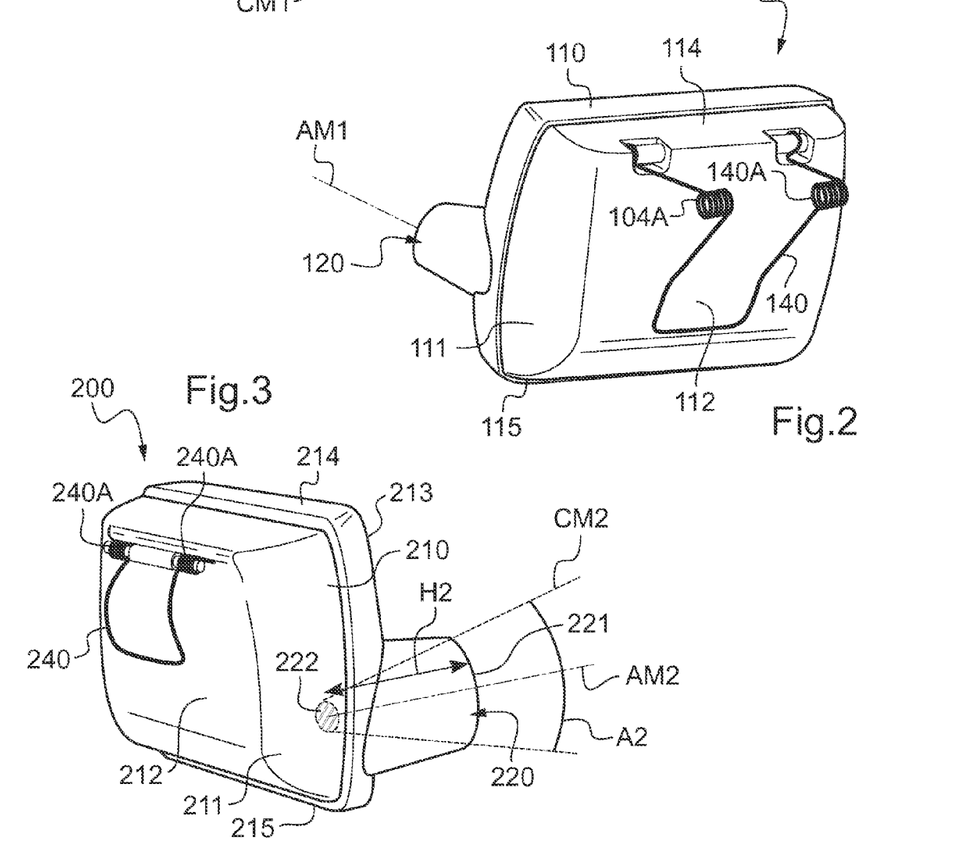
FIG. 2 is a rear perspective view of the FIG. 1 measurement device.
FIG. 3 is a rear perspective view of a first variant of the FIG. 1 measurement device.

The clip means 140 of the measurement support shown in FIGS. 1 and 7 can be seen more clearly in FIG. 2, and in this example they comprise an arrangement of two torsion springs 140A connected to a rigid metal wire that forms an attachment clip that extends from the rear face 112 of the box 111 of the measurement support 110.

The springs 140A in this example are spaced apart from the rear face 112 of the box 111 of the measurement support 110 so as to enable the measurement support 110 to be fastened on a reading medium that presents considerable thickness.

In a first variant of this first embodiment, as shown in FIG. 3, the clip means 240 likewise comprise an attachment clip formed by two torsion springs 240A. In this example the torsion springs 240A are located close to the rear face 212 of the box 211 of the measurement support 210 and allow the measurement support 210 to be fastened only on a reading medium that presents thickness smaller than in the first embodiment as shown in FIG. 2.

The reading medium may for example be a computer screen similar to that shown in FIG. 7.

In a second variant of the first embodiment, as shown in FIGS. 4 and 5, said mounting means comprise two hooks 340 mounted on the rear face 312 of the box 311 of the measurement support 310 and open towards the bottom face of the measurement support 300. Each hook 340 has a rectilinear support branch rotatably mounted on the rear face 312 of the box 311, thereby enabling each hook at least to pivot between a folded position in which it lies in a plane that is substantially parallel to the rear face 312 of the box 311 of the measurement support 310, and a deployed position in which it extends in a plane substantially perpendicular to the rear face 312 of the box 311.

Each hook 340 also has a central branch of length that determines the maximum thickness of the reading medium 330 on which the measurement support can be mounted. This central branch includes a return portion at its free end enabling it to be hooked onto the reading medium 330.

As shown in FIG. 4, the hook 340 may be adjusted to the thickness of the reading medium 330 if said thickness is less than the maximum thickness, merely by pivoting the hook through an appropriate angle about the support branch. By way of example, the reading medium 330 may be a computer screen similar to that shown in FIG. 7.

In a third variant of the first embodiment, as shown in FIG. 6, the measurement support 410 includes a stand 440 enabling the measurement support 410 to be stood in stable manner on a reading medium 430.

In this example the stand is retractable: it pivots between a position in which it is received inside the box 411 of the measurement support 410, and a position in which it is deployed out from the box.

In this example, the reading medium 430 may be constituted by a table on which a sheet is placed having signs thereon to be read by the individual.

Finally, in a fifth variant of the first embodiment (not shown), the measurement support may be fastened to any support that is not necessarily a reading medium, for example a wall, and the individual holds by hand or gazes on a reading medium that is not mechanically connected to the measurement support.

In general, the reading medium 130, 330, 430 has on its front face, i.e. on its side that is to face towards the individual's head 10, a plane display portion 131, 331, 431 having displayed thereon signs at which the individual gazes while a measurement is being taken.

The signs are typically aligned to constitute a plurality of display lines, e.g. comprising optotypes similar to those used by opticians for evaluating an individual's vision defects. It may also be constituted by any text that the individual reads.

This display portion 131, 331, 431 may comprise stationary signs or a dynamic display screen enabling different signs to be displayed, e.g. enabling texts to be displayed in which the letters used present different heights, or texts in different languages.

The reading medium 130, 330, 430 is preferably portable and the individual holds it in the hands while a measurement is being taken (see FIG. 7).

Nevertheless, it may be useful to make the reading medium non-removable, e.g. in order to avoid the reading medium being stolen from the optician's office.

Under such circumstances, it may for example be mounted on an arm enabling its position in three dimensions in front of the individual to be adjusted, in particular concerning the distance in a horizontal plane between the reading medium and the individual's head, and the height in a vertical plane between the reading medium and the individual's head, and also the inclination of the reading medium about a horizontal axis.

The individual may then adjust the position of the reading medium by hand by causing those various parameters to be varied, or may make such adjustments under remote control, or may indeed give instructions to an operator so as to enable the reading medium to be placed in a reading position that is comfortable for the individual.

The individual preferably adjusts the relative position of the reading medium and the individual's head so as to occupy a reading position that is natural and comfortable.

Figures 9, 10:
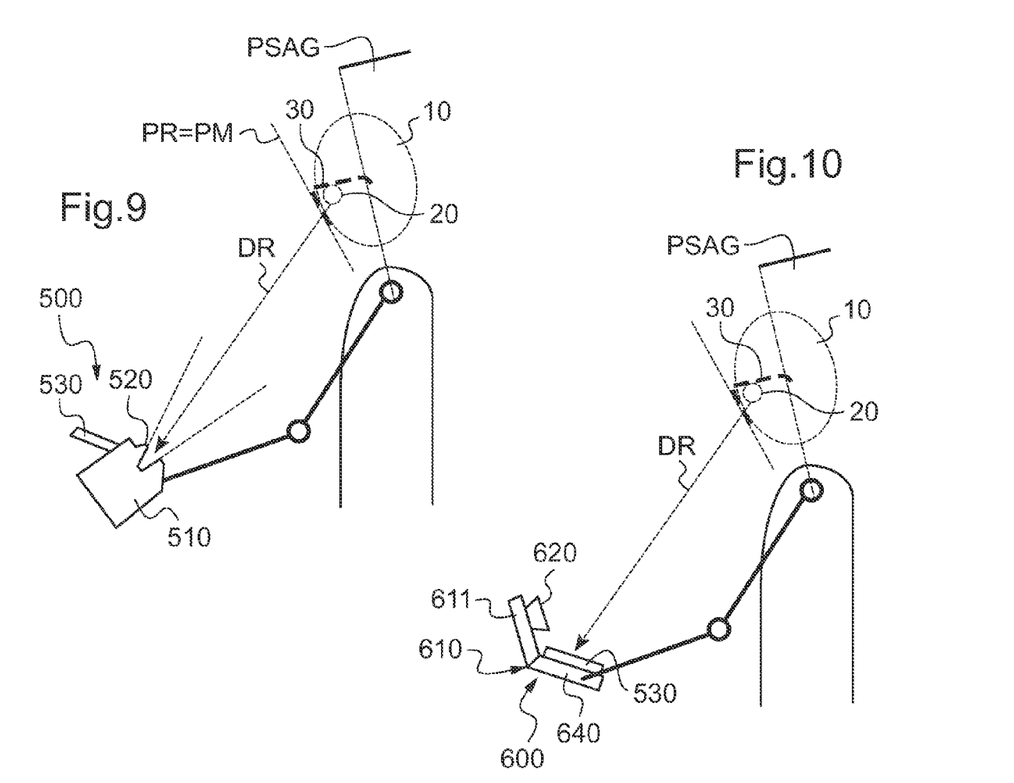
FIG. 9 is a diagrammatic view of an individual using the FIG. 8 device.
FIG. 10 is a view analogous to FIG. 9, showing a second variant of the second embodiment of the measurement device of the invention.
Figure 11:
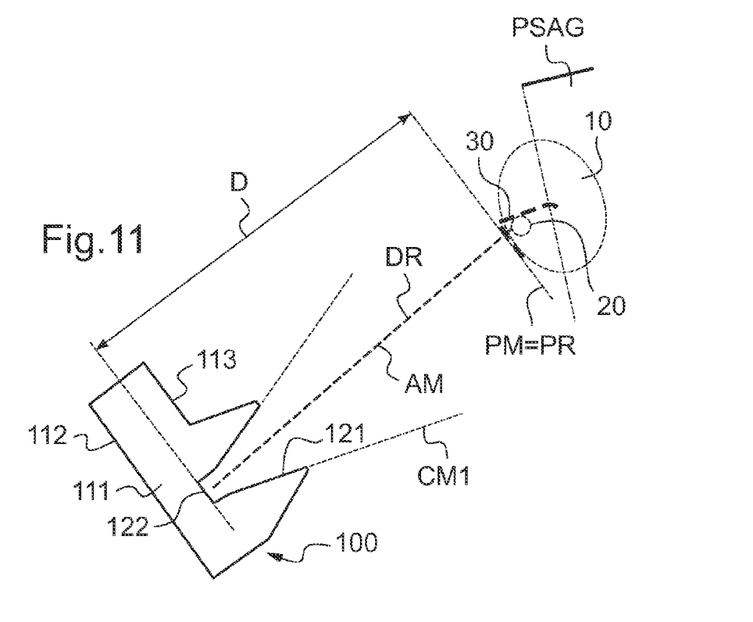
FIG. 11 is a diagrammatic profile view in elevation of an individual using the FIG. 1 device.

In a second embodiment of the device of the invention, shown in FIGS. 8 to 10, the measurement device 500, 600 comprises a reading medium 530 that presents a plane display portion 531 suitable for displaying signs, together with means for removably mounting the reading medium 530 on the measurement support 510, 610. The reading medium 530 may for example be a portable telephone or a multimedia tablet that is provided by the optician or that belongs to the individual.

In a first variant of this second embodiment, shown in FIGS. 8 and 9, the measurement support 510 forms a docking station for the reading medium 530.

The box 511 of the measurement support 510 then forms a base suitable for standing in stable manner on a plane that is horizontal or slightly sloping, such as the top of a table, and it includes mechanical connection means suitable for co-operating with complementary mechanical connection means of the reading medium, in such a manner that, once connected, the plane of the display portion 531 of the reading medium 530 slopes relative to the plane on which the base 511 stands, i.e. is inclined at an angle of less than 90 degrees less than said plane. The base-forming box 511 may thus, in operation, stand on a table or be held in the hand by the individual in order to optimize reading comfort, as shown in FIG. 9.

The mechanical connection means comprise a housing 540 formed in a setback in the horizontal top face of the box 511 and suitable for receiving and holding a bottom portion of the reading medium 530. The reading medium 530, when connected, thus extends above the box 511 of the measurement support 510 and its emitter-receiver members 520.

In a second variant of this second embodiment, as shown in FIG. 10, the box 611 of the measurement support 610 is carried by a base 640 suitable for standing in stable manner on a plane that is horizontal or slightly sloping, such as the top of the table, and it includes mechanical connection means suitable for co-operating with complementary mechanical connection means of the reading medium 530. These mechanical connection means (not shown) of the base 640 are typically implemented in the form of clip means or means for holding the reading medium 530 in close-fitting or tight manner.

The box 611 of the measurement support 610 forms an L-shape with the base 640 such that the emitter-receiver members 620 are located above the base 640 and the reading medium 530. Advantageously, provision can be made for the box 611 to be hinged to the base 640 about a horizontal axis.

Specifically, the reading medium is received flat on the base 640 in such a manner that the plane of its display portion 531 is parallel to the plane on which the base 640 is suitable for standing. In operation, the base 640 may thus stand on a table or may be held in the hand by the individual for optimized reading comfort, as shown in FIG. 10.

In both variants of this second embodiment, the measurement support 510, 610 may also include electronic and computer connection means for connection with the reading medium 530. The measurement support 510, 610 may then communicate with the reading medium 530. By way of example, it is then possible to provide for adjusting the size of the signs displayed on the reading medium 530 as a function of the reading distance as measured by the measurement support 510, 610.

Whatever the embodiment of the measurement device 100, 200, 300, 400, 500 of the invention, it includes an electronic processor unit suitable for responding to the ultrasound signal received by at least one of the emitter-receiver members 120, 220, 320, 420, 520, 620 to deliver a signal representative of the distance D between the eyeglass frame 30 on the individual's head 10 (FIG. 10) and the measurement support 100, 200, 300, 400, 500 and to deduce therefrom the looked-for characteristic reading distance.

Preferably, the electronic processor unit is suitable for deducing the looked-for characteristic reading distance from the signals delivered by at least one of the two emitter-receiver members 120, 220, 320, 420, 520, 620 and preferably by both of them.

The measurement device 100, 200, 300, 400, 500 also includes means for verifying that the frame 30 is situated at least in part in the measurement cone CM1, CM2, CM3, CM4, CM5 of the emitter-receiver member under consideration.

Whatever the embodiment of the measurement device, the measurement members 120, 220, 320, 420, 520, 620 may either be mounted in stationary manner on said measurement support 110, 210, 310, 410, 510, or else they may be movably mounted on the measurement support 110, 210, 310, 410, 510 so as to be capable at least of pivoting about a pivot axis perpendicular to their measurement axes AM1, AM2, AM3, AM4, AM5. Under such circumstances, it is possible to envisage that a single measurement member is movably mounted on the measurement support.

In the examples shown in the accompanying figures, the emitter-receiver members 120, 220, 320, 420 of the measurement devices in the first embodiment and its variants are mounted in stationary manner on the measurement support 110, 210, 310, 410, whereas the emitter-receiver members 520, 620 of the measurement device 500, 600 described with reference to FIGS. 8 to 10 for both variants of the second embodiment are movably mounted on the measurement support 510, 610 in order to pivot about the pivot axis X that is perpendicular to the measurement axes AM5 of the emitter-receiver members 520, 620.

In the first embodiment, the means for verifying that the individual's head is situated at least in part in the measurement cone of said main measurement member comprise visual detection means 160, 360 enabling the individual to detect visually when the individual's head is in a position relative to the main measurement member such that the head is situated at least in part in the measurement cone of said main measurement member.

By way of example, the visual detection means 160 comprise, as shown in FIG. 1, a target 162 and a mark 161 carried by the measurement support 110 and secured to emitter-receiver members 120, the mark 161 and the target 162 being offset in the common direction of the measurement axes AM1 of the emitter-receiver members 120.

The target 162 and the mark 161 are arranged in such a manner as to be perceived visually by the individual as being centered relative to each other only when the individual's head is situated at least in part in the measurement cone of said main measurement member. This is due to a parallax effect that results from the mark 161 and the target 162 being offset along the direction of the measurement axes AM1.

In this example, the target 162 is constituted by a circle 162 that lies in a plane parallel to the front face 113 of the measurement support 110 that faces the individual, being set back from said front face 113. The target 162 can be seen by the individual through a transparent window 163 of the box 111.

By way of example, the mark 161 is an opaque disk that is stuck to the window 163.

In a variant, other target and mark pairs could be used: a circle at the center of the square; a circle between two parallel lines; or two concentric circles, for example.

Alternatively, and as shown in FIG. 4, the visual detection means comprise at least one target 362 forming part of the measurement support and thus secured to the emitter-receiver members. The target 362 can be seen by the individual only when the individual's head is situated at least in part in the measurement cone of said main measurement member.

The target 362 is preferably a source of light of the light-emitting diode (LED) type that is located at the end of a cylindrical cavity 361 that opens out into the front face 313 of the box of the measurement support, so as to be visible to the individual solely when the individual's gaze direction DR extends along the longitudinal axis Y of the cylindrical cavity 361, this gaze direction corresponding to a relative position of the individual's head 10 and of the measurement support 310 in which the individual's head is situated at least in part in the measurement cone CM3 of the emitter-receiver members.

In a variant, the target is a sign displayed by a display screen and visible only when the individual's gaze is at an angle of incidence such that when the individual looks at the target at said angle of incidence the individual's head is situated at least in part in the measurement cone of said main measurement member.

In practice, in order to use these variants of the first embodiment, the individual places the measurement support 110, 210, 310, 410 on its reading medium 130, 330, 430 and takes up a natural reading position in order to read the signs displayed on the display portion of the reading medium.

Thereafter, the individual looks towards the measurement support 110, 210, 310, 410 without moving the head and adjusts the position of the measurement support relative to the reading medium, and optionally the position of the reading medium, so as to center the target 162 and the mark 161 for the measurement device 100 shown in FIGS. 1 to 7, or so as to see the light-emitting target 362 in the measurement device 300 shown in FIGS. 4 and 5.

The distance D between the measurement support and the individual's eyeglasses is then measured. This step is described in greater detail below.

Finally, the individual looks at the display portion of the reading medium. In a variant, provision may advantageously be made for the distance D to be measured after the individual has gone back to looking at the display portion of the reading medium.

In the second embodiment, the means for verifying that the individual's head 10 is situated at least in part in the measurement cone CM5 of at least one of the emitter-receiver members 520 comprise automatic detection means for automatically detecting a relative position of the individual's head and the emitter-receiver member 520 in question in which the head is situated at least in part in the measurement cone CM5 under consideration.

In this example, the emitter-receiver members 520 are mounted to pivot together on the measurement support 510. These automatic detection means thus include means for scanning these emitter-receiver members 520 over a range of angular positions relative to the measurement support 510, and means for determining the angular position of the emitter-receiver members 520 that corresponds to a received ultrasound signal of maximum intensity or intensity greater than a threshold.

To do this, while emitting ultrasound, the scan means cause the emitter-receiver members 520 to pivot so that the measurement axis AM5 of each emitter-receiver member 520 scans the individual's head 10. The scanned range of angular positions covers at least 15 degrees towards the front or towards the rear of the measurement support 510 relative to a reference mean angular position in which the angle GAMMA formed between the measurement axis of the receiver member and the front face 513 of the box 511 of the measurement support 510 lies in the range 10 degrees to 80 degrees (FIG. 8).

Scanning is preferably performed automatically: the pivoting of the measurement members 520 is then motor-driven and under the control of electronic control means.

The scanning may also be performed manually by the individual. The measurement support then includes manual pivot means such as a knob.

Automatic scanning presents the advantage of not involving the individual.

Said electronic processor unit processes the detected ultrasound signals as a function of the angular position of the emitter-receiver members 520 and deduces therefrom the looked-for measurement angular position.

In particular, the measurement angular position corresponds to the position in which an intensity maximum is detected in the ultrasound signals.

Alternatively, the measurement angular position corresponds to the position in which the intensity of the ultrasound signal is greater than a threshold.

By way of example, the threshold may correspond to a percentage of the maximum intensity of the ultrasound signal as obtained during a calibration step.

The ultrasound emission duration at the end of which the maximum signal intensity is detected is generally less than or equal to 40 seconds.

The electronic control means for controlling the motor-driven scan means then cause the emitter-receiver members 520 to pivot towards that angular position.

Once the emitter-receiver members are in the measurement angular position, ultrasound emission is triggered and the ultrasound signal is detected.

Measurement can thus be performed quickly and easily.

When scanning is performed manually, a sound or light signal indicates when the measurement angular position has been reached, for example.

In practice, in order to use this second embodiment, the individual places the reading medium 530 on the measurement support 510 and takes up a natural reading position for reading the signs displayed on the display portion of the reading medium 530.

Thereafter, the automatic or manual step of scanning the emitter-receiver members 520 over the angular range is then performed. The looked-for angular position is determined by the electronic processor unit and the emitter-receiver members 520 are moved into this position either automatically, or manually by the individual.

The distance D between the measurement support and the individual's eyeglasses is then measured.

In a third embodiment derived from the first embodiment, it is possible to provide for the measurement support to be mounted on the reading medium with a degree of freedom to move in pivoting about an axis that is perpendicular to the measurement axes of the emitter-receiver members. By way of example, the measurement support is then mounted to pivot on an intermediate part that includes the clip means or the hooks for releasably mounting the reading medium.

The means for verifying that the individual's head is situated at least in part in the measurement cone of said main measurement member may then comprise automatic detection means comprising means for causing the emitter-receiver members to scan over a range of angular positions relative to the measurement support, the scanning being performed either manually by the individual causing the measurement support to pivot by acting directly thereon, or automatically if the pivoting of the measurement support is motor-driven. The automatic detection means also include means for determining the measurement angular position of the emitter-receiver members that corresponds to receiving an ultrasound signal at maximum intensity or at intensity greater than a threshold.

For this purpose, while ultrasound is being emitted, the scan means cause the measurement support to scan so that the measurement axis of each emitter-receiver member scans the individual's head. The range of scanned angular positions covers at least 15 degrees towards the front or the rear of the measurement support relative to a reference mean angular position in which the angle between the measurement axis of the receiver member and the display portion of the reading medium lies in the range 10 degrees to 80 degrees.

The scanning is preferably performed automatically: pivoting is then motor-driven and controlled by electronic control means.

The operation of the measurement device remains similar to that described for the second embodiment.

In general, the means for verifying that the individual's head is situated at least in part in the measurement cone of at least one of the emitter-receiver members are preferably arranged to verify that the measurement axis of the emitter-receiver member is substantially perpendicular to the plane PM of the eyeglass frame worn by the individual. In this configuration, the ultrasound signal reflected on the frame and the ophthalmic lenses and received by the emitter-receiver member in question is at a maximum and the measurement is thus more accurate.

Whatever the embodiment of the measurement device, the electronic processor unit for processing the ultrasound signal received by the emitter-receiver members of the measurement device 100, 200, 300, 400, 500 is suitable for responding to the signal received by the emitter-receiver members by delivering a signal that is representative of the distance between the measurement support 110, 210, 310, 410, 510 and the frame 30 (as in the example described) or the lenses (in an analogous version that is readily described therefrom) of the eyeglasses worn on the individual's head 10, and to deduce therefrom said characteristic reading distance.

The processor unit begins by determining the distance D between the measurement support 110, 210, 310, 410, 510 and the individual's eyeglass frame 30, referred to below as the measurement distance D.

The electronic processor unit is suitable for extracting from the ultrasound signal received by the receiver member that portion of said signal that is reflected by the lenses or the eyeglass frame carried by the individual, to the exclusion of the portion of said signal that is reflected by the individual's skin.

The intensity of the received signal depends on the nature of the material that reflected the emitted ultrasound signal, and on the difference between the angular position of the measurement axis of the emitter-receiver members and the measurement angular position in which said measurement axis is perpendicular to the mean plane of the frame. The measurement angular position thus corresponds to a maximum intensity received ultrasound signal.

The absolute amplitude of the received signal, i.e. its strength or intensity, makes it possible to determine whether the received signal comes from a reflection on the individual's skin, or from a reflection on the eyeglass frame.

By way of example, for a distance D of about 40 centimeters, the signal received after reflection on the frame is about four times stronger than the signal received after reflection on the skin.

It is thus possible to distinguish the signal received after reflection on the eyeglass frame from the signal received after reflection on the skin, with this remaining possible even when the angular position of the measurement axis of the emitter-receiver members is not exactly the measurement angular position.

The electronic processor unit of the measurement device performs automatic gain control, i.e. it adjusts the amplification of the signal received by the receiver or emitter-receiver element, as a function of the amplitude of the received signal.

This amplitude depends in particular on the area of the eyeglasses worn by the individual. A small eyeglass frame will give rise to a received signal of amplitude that is smaller than an eyeglass frame of larger size.

The electronic processor unit of the measurement device increasing the amplification of this signal serves to compensate for this difference.

In addition, in the event of a very intense signal peak, of amplitude greater than a first predefined threshold value, the electronic processor unit is programmed to peak-limit the signal prior to performing gain control.

The electronic processor unit of the measurement device detects the received signal of intensity greater than a second predetermined threshold value. This second threshold value preferably corresponds to an intensity value of the signal that ensures that the received signal comes from a reflection of the emitted signal on the frame of the individual's eyeglasses.

This second threshold value is determined from calibration measurements performed beforehand or it corresponds to a predetermined standard value relative to the maximum expected signal for a frame of given size and for determined gain. By way of example, this standard value is taken to be equal to 20 percent of the maximum signal.

A plurality of threshold values lower than the second threshold value may be provided to take account of the decrease in the intensity of the received signal as a function of the difference between the angular position of the measurement axes of the emitter-receiver members and the measurement angular position.

Detection is then performed at these various threshold values in succession by the electronic processor unit of the measurement device in the event of a failure to detect a signal above the second threshold value. The other threshold values are applied in decreasing order until a signal is detected.

This thresholding technique serves to avoid failures of detection, which would make it necessary to perform a new measurement.

If the received signal presents intensity below the lowest threshold value, then the measurement device issues an error message indicating that the measurement must be repeated.

Under ideal circumstances in which the receiver element receives only a signal reflected by the individual's eyeglasses, the signal received as a function of time presents a square waveform.

In reality, the ultrasound signal received after reflection on the wearer's head includes a component at shorter times corresponding to the signal reflected by the individual's skin situated in front of the eyeglasses, followed by a component at intermediate times corresponding to the signal reflected by the individual's eyeglasses, and finally a component at longer times corresponding to the signal reflected by the individual's skin situated behind the eyeglasses relative to the measurement support.

The signal received by the receiver or emitter-receiver members then presents an approximately flat shape that is associated with the texture of the surface on which the ultrasound signal is reflected.

The means processing the received signal then perform a step of detecting the signal reflected by the frame or the correcting lenses of the eyeglasses carried by the individual. For this purpose, they perform a correction to the slope of the real received signal by amplifying said slope so as to approach the ideal situation and determine accurately the moment at which the signal reflected on the individual's eyeglasses was received.

By way of example, this moment is determined as being the time that corresponds to a threshold of the rising slope of the received signal, which threshold is settable (typically being situated between half-height and 20 percent of the height).

A first value for the measurement of the distance between the individual's eyeglasses and the emitter-receiver members of the measurement support is then determined as a function of said time.

Preferably, once a first value has been determined for the measurement distance, the received signal is also subjected to a calibration correction step corresponding to subtracting a reference signal corresponding to the signal as received when the ultrasound is reflected by the skin.

This reference signal corresponds to the signal received by the receiver or emitter-receiver member after reflection on the skin of the face of a mean reference individual when the reference individual is at a distance from the measurement device that is equal to the first value of the measurement distance.

By way of example, this reference signal is determined by performing three calibration measurements at known measurement distances, e.g. at measurement distances of 30 centimeters, 40 centimeters, and 50 centimeters.

Linear interpolation of said signals makes it possible to deduce a reference signal for all measurement distances lying in the range 30 centimeters to 50 centimeters.

The electronic signal processor unit subtracts from the received signal the reference signal that corresponds to the first value determined for the measurement distance.

Thereafter, the above steps are repeated on the corrected signal so as to determine a second value for the measurement distance that is more accurate than the first.

The accuracy of the measurement distance as determined in this way is about 1 centimeter to 2 centimeters.

The total duration of measurement is about 1 minute. This measurement is thus performed very quickly.

More particularly in this example, a mean first measurement distance between the measurement support and the individual's eyeglasses is determined from the mean of the ultrasound signal detected by the two emitter-receiver members 120, 220, 320, 420, 520 of the measurement support 110, 210, 310, 410, 510 and that is processed by the electronic processor unit as explained above.

The two emitter-receiver members of the measurement support are each located facing a respective one of the ophthalmic lenses of the individual's eyeglass frame 30, and thus each of them measures a measurement distance between one of the ophthalmic lenses of said frame 30 and the corresponding emitter-receiver member.

The first mean measurement distance between the measurement support and the eyeglasses thus corresponds to a mean of the distances between each of the lenses and the measurement support.

Taking this mean serves to limit the influence on the measurement of a small amount of rotation of the head about a vertical axis: this serves to limit the error introduced by the fact that the sagittal plane PSAG of the wearer's head does not coincide exactly with the plane of symmetry PS of the measurement device.

Preferably, the measurements are repeated and averaged: the distance between the measurement support and the eyeglasses is determined from the mean of at least five first mean measurement distances as determined in this way.

In a variant, the electronic processor unit determines two distances between the measurement support and the eyeglass from the ultrasound signals received by each of the two emitter-receiver members, corresponding respectively to measuring the distance between each of the ophthalmic lenses and the measurement support. Thereafter the electronic processor unit averages these two distances in order to determine a value for the looked-for distance between the measurement support and the eyeglasses. A plurality of these values may subsequently be averaged.

This makes the measurement more accurate.

The electronic processor unit then deduces from said measurement distance the looked-for characteristic reading distance of the individual.

To do this, the processor unit corrects the distance between the measurement support and the eyeglasses as determined beforehand as a function of the relative position of the measurement support and of the reading medium.

In a first possibility, the measurement device includes means for keeping the position of the reading medium relative to the measurement support unchanged, and the electronic processor unit is suitable for calculating said characteristic reading distance as a function of said unchanged position.

For example, it is possible to envisage that the position of the measurement support relative to the reading medium is predetermined and constant. This applies for example in the second embodiment of the device as shown in FIG. 8.

This also applies in the first embodiment of the device as shown in FIGS. 1 to 6 providing the measurement support is always placed on the reading medium at the same distance from the display portion of said reading medium. The mechanical means for ensuring that the position of the reading medium relative to the measurement support is unchanging may then, for example, be abutment means placed on the reading medium in order to limit the positions in which the measurement support can be mounted on the reading medium.

Under such circumstances, it is possible to store relative position parameters in a memory of the electronic processor unit, such as the relative inclination and the distance between the reading medium and the measurement support. The measurement unit is then programmed to determine the looked-for characteristic reading distance that corresponds to the distance between the eyeglasses and the reading medium as a function of the distance between the eyeglasses and the measurement support, and as a function of said parameters.

It is also possible to envisage that the position of the measurement support relative to the reading medium is adjustable. The measurement device then includes means for determining the position of the reading medium relative to the measurement support in a measurement direction.

By way of example, these means may in particular comprise means for measuring an angle of inclination of the measurement support relative to the horizontal and means for measuring the distance between the measurement support and the reading medium. By way of example they may comprise at least one inclinometer on board the measurement support. It is also possible to provide a second inclinometer on board the reading medium.

When the measurement support is mounted on a support other than the reading medium, e.g. a wall, it is also possible to envisage that the electronic processor unit is programmed to deduce from the received ultrasound signal the distance between the eyeglasses and the measurement support, and also the distance between the reading medium and the measurement support, by performing processing similar to that described above.

The electronic processor unit can then correct the distance between the eyeglasses and the measurement support as determined as a function of the distance between the reading medium and the measurement support in order to deduce therefrom the looked-for distance between the eyeglasses and the reading medium.

The measurement support also optionally includes wired or wireless means for transmitting the distance measurement it has performed to one or more other devices used by the optician, in particular to the reading medium.

By way of example, the electronic processor unit may then be suitable for controlling the reading medium to modify the size of the displayed signs as a function of the determined characteristic reading distance.

In particular, the measurement support may be a measurement unit forming part of some greater measurement kit.

The measurement support may also include means 170, 370, 570 for displaying the determined characteristic reading distance, as shown in FIGS. 1, 5, and 8. This distance can then be read directly from the measurement device by the individual or by the optician.

The measurement support 110, 210, 310, 410, 510 preferably includes independent power supply means, e.g. optionally rechargeable batteries.

The present invention is not limited in any way to the embodiments described and shown, and the person skilled in the art knows how to provide any variant thereto in accordance with its spirit.

In a variant, the means for verifying that the eyeglass frame is situated at least in part in the measurement cone of said main measurement member may also include a mirror placed on the front place of the measurement support and in which the individual should be able to see his or her own eyes.

The invention claimed is:

1. A device (500, 600) for measuring a characteristic reading distance of an individual, the device comprising:
    a measurement support (510, 610) that includes a box (511, 611) carrying at least one ultrasound emitter member (520, 620) and at least one ultrasound receiver member (520, 620), at least one of these members, referred to as a main measurement member (520, 620) having a measurement element (522) in a cavity (521) in the box and possessing a measurement axis (AM5) on which emission or reception by the main measurement member (520, 620) has a maximum intensity, and being suitable for emitting or receiving ultrasound propagating in a measurement cone (CM5) centered on its measurement axis (AM5),
    an electronic processor unit adapted, as a function of the ultrasound signal received by the receiver member (520, 620), to deliver a signal that is representative of the distance (D) between the measurement support (510)

and an eyeglass frame (30) worn by the individual's head (10), and to deduce therefrom said characteristic reading distance, means to verify that said eyeglass frame is situated at least in part in the measurement cone of said main measurement member, a reading medium (530) presenting a plane display portion suitable for displaying signs, and means (540) for releasably mounting the reading medium (530) on the measurement support (510, 610), wherein said measurement support (510, 610) forms a docking station for the reading medium (530), the docking station including both a base (511, 640) suitable for standing in stable manner on a plane, and releasable mechanical connection means (540) suitable for co-operating with complementary connection means of the reading medium.

2. The device according to claim 1, wherein the electronic processor unit is suitable for calculating said characteristic reading distance as being the distance between said reading medium (530) and the eyeglass frame (30) worn by the individual's head (10).

3. The device according to claim 1, wherein said main measurement member is mounted stationary on said measurement support.

4. The device (500) according to claim 1, wherein said main measurement member (520) is mounted to be movable on said measurement support (510) so as to be capable at least of pivoting relative to a pivot axis (X) perpendicular to the measurement axis (AM5) of said main measurement member (520).

5. The device (500) according to claim 4, wherein the means for verifying that the individual's head is situated at least in part in the measurement cone of said main measurement member include automatic detection means for automatically detecting a position of the individual's head (10) relative to the main measurement member (520), in which the head (10) is situated at least in part in the measurement cone (CM5) of said main measurement member (520), said automatic detection means including means for causing said main measurement member (520) to scan through a range of angular positions relative to the measurement support, and means for determining the angular position of said main measurement member (520) that corresponds to a received ultrasound signal of maximum intensity or intensity greater than a threshold.

6. The device (500, 600) according to claim 1, including mechanical means for ensuring that the position of the reading medium (530) relative to the measurement support is unchanging and in which the electronic processor unit is suitable for calculating said characteristic reading distance as a function of said unchanging position.

7. The device (500, 600) according to claim 1, wherein the electronic processor unit controls the reading medium to modify the size of the signs displayed as a function of the determined characteristic reading distance.

8. The device (500, 600) according to claim 1, wherein the receiver member (520, 620) includes a receiver element (522) placed inside the cavity (521) that is conical and presents an angle at the apex (A5) lying in the range 15 degrees to 45 degrees, and at a depth (H5) of at least 30 millimeters.

9. The device (500, 600) according to claim 1, wherein the electronic processor unit is suitable for extracting from the ultrasound signal received by the receiver member (520, 620), that portion of said signal that is reflected by the lenses or the frame of eyeglass worn by the individual, to the exclusion of the portion of said signal that is reflected by the individual's skin.

* * * * *